(12) United States Patent
Schmidt et al.

(10) Patent No.: US 6,649,354 B1
(45) Date of Patent: Nov. 18, 2003

(54) CATALYTICALLY GENERATED MASS LABELS

(75) Inventors: Gunter Schmidt, Houghton (GB); Andrew Hugin Thompson, Alloway (GB)

(73) Assignee: Xzillion GmbH & Co., Frankfurt (DE)

( * ) Notice: Subject to any disclaimer, the term of this patent is extended or adjusted under 35 U.S.C. 154(b) by 0 days.

(21) Appl. No.: 09/508,049
(22) PCT Filed: Sep. 7, 1998
(86) PCT No.: PCT/GB98/02690
§ 371 (c)(1),
(2), (4) Date: May 30, 2000
(87) PCT Pub. No.: WO99/13103
PCT Pub. Date: Mar. 18, 1999

(30) Foreign Application Priority Data

Sep. 5, 1997 (GB) .............................. 9718921

(51) Int. Cl.[7] .................. G01N 33/53; G01N 33/543
(52) U.S. Cl. .................. 435/7.1; 435/4; 435/6; 435/7.9; 435/7.92; 435/28; 435/174; 435/176; 435/177; 435/320.1; 435/814; 436/164; 436/507; 436/513; 436/518; 436/524; 436/528; 436/536; 436/538; 436/805; 436/823; 436/824; 422/68.1; 530/810; 530/811
(58) Field of Search ................ 435/320.1, 7.1, 435/28, 6, 4, 7.9, 7.92, 174, 176, 177, 8; 436/513, 518, 507, 524, 528, 536, 538, 164, 805, 823, 824; 530/810, 811; 422/68.1

(56) References Cited

U.S. PATENT DOCUMENTS

| | | | | |
|---|---|---|---|---|
| 4,016,043 A | * | 4/1977 | Schuurs et al. .......... 195/103.5 |
| 4,444,879 A | * | 4/1984 | Foster et al. ............... 435/7.95 |
| 4,780,421 A | * | 10/1988 | Kameda et al. ............. 436/518 |
| 4,868,105 A | * | 9/1989 | Urdea et al. .................... 435/6 |
| 5,162,218 A | * | 11/1992 | Schultz ....................... 435/188 |
| 5,380,650 A | * | 1/1995 | Barnard et al. ............... 435/28 |
| 5,716,825 A | | 2/1998 | Hancock et al. |
| 6,110,676 A | * | 8/2000 | Coull et al. ..................... 435/5 |
| 6,383,742 B1 | * | 5/2002 | Drmanac et al. ......... 435/287.2 |

FOREIGN PATENT DOCUMENTS

| | | | |
|---|---|---|---|
| WO | WO 9117442 | * 11/1991 | ................. 33/529 |
| WO | WO 94/16101 | 7/1994 | |
| WO | WO 95/04160 | 2/1995 | |
| WO | WO 97/27331 | 7/1997 | |
| WO | WO 98/26095 | 6/1998 | |
| WO | WO 98/31830 | 7/1998 | |
| WO | WO 98/48047 | 10/1998 | |

OTHER PUBLICATIONS

Kricka Clinical chemistry 40/3 347–357 (1994).*
Feucht et al Jornal of Virological Methods 55 (1995) 105–110.*
Lutz et al Journal of Chromatography A 755 (1996) 179–187.*
Voet et al Biochemistry(1990).*

* cited by examiner

Primary Examiner—Christopher L. Chin
Assistant Examiner—Kartic Padmanabhan
(74) Attorney, Agent, or Firm—Burns, Doane, Swecker & Mathis, LLP

(57) ABSTRACT

The present invention involves a method for assaying a substance. The method of the present invention comprises contacting the substance with an assay agent comprising a catalytic agent to associate the substance with the catalytic agent, contacting the resulting associated substance with a label precursor capable of reacting catalytically with the catalytic agent to release the label, and detecting a mass label. The present invention also involves a kit for assaying a substance. The kit of the present invention comprises an assay agent comprising a catalytic agent, and a label precursor capable of reacting catalytically with the catalytic agent to release a mass label.

13 Claims, 3 Drawing Sheets

Orthogonal TOF geometry

CATALYTICALLY GENERATED MASS LABELS

CROSS-REFERENCES TO RELATED APPLICATIONS

This application is a 371 of PCT/GB98/02690, filed Sep. 7, 1998.

BACKGROUND OF THE INVENTION

1. Field of the Invention

This invention relates to a method for assaying a substance which is present in a very low concentration. Specifically, this invention concerns a method which employs catalysis to amplify a signal. The method is especially suited to biological assays. The invention has the further advantage that it allows the simultaneous assay of a mixture comprising a plurality of substances, even when these substances are present in very low quantities.

2. Description of the Related Art

Biological assays must often achieve a sensitivity to target molecules in the low femotomolar to attomolar range. Assays based on ligand binding can achieve this but often require signal amplification to indicate the success of the ligand binding in a detectable manner. Radio-isotope labelled ligands can achieve this but there are safety implications in using radio-active agents which makes them dangerous and expensive to use. Furthermore, since there is no trivial or cheap way to differentiate between different kinds of radiation, only one radiolabelled ligand can be used in any one assay.

BRIEF SUMMARY OF THE INVENTION

Colorimetric, chemoluminescent assays and fluorescence based systems permit signal amplification in a variety of systems, however the number of labels that can be used simultaneously is limited due to spectral overlap effects of emission based systems.

An object of the present invention is to solve the above problems. Accordingly, the present invention provides a method for assaying a substance, which method comprises contacting the substance with an assay agent comprising a catalytic agent to associate the substance with the catalytic agent, contacting the resulting associated substance with a label precursor, and detecting a label, wherein the label precursor is capable of reacting catalytically with the catalytic agent to release the label, and wherein the label is a mass label.

The present invention also provides a kit for assaying a substance, which kit comprises an assay agent comprising a catalytic agent, and a label precursor capable of reacting catalytically with the catalytic agent to release a label, wherein the label is a mass label.

BRIEF DESCRIPTION OF THE SEVERAL VIEWS OF THE DRAWINGS

The invention will now be described in further detail by way of example only, with reference to the accompanying drawings, in which.

DETAILED DESCRIPTION OF THE INVENTION

Figure 1:
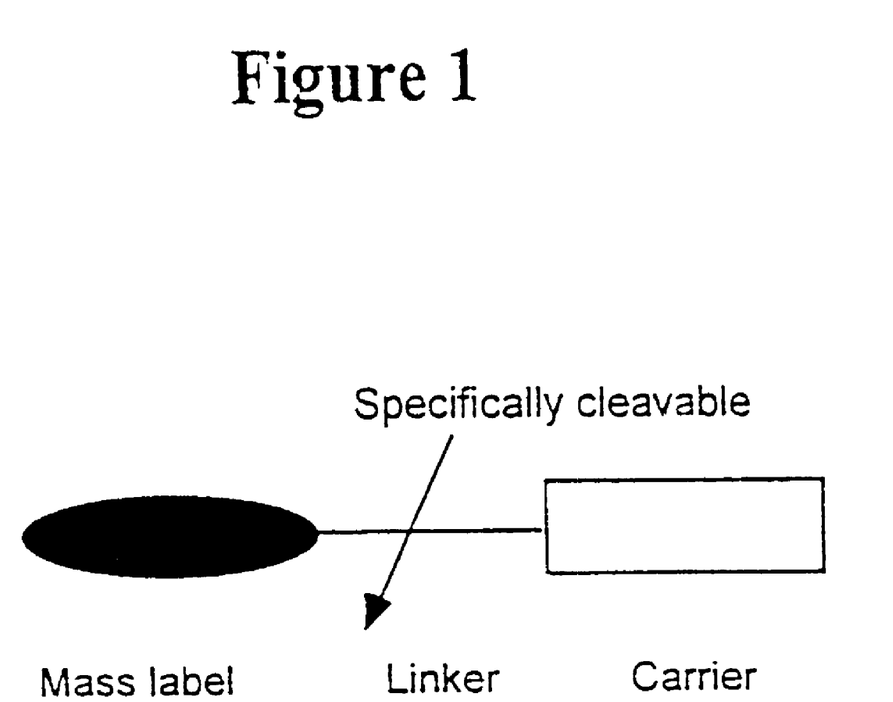
FIG. 1 shows a label precursor (secondary signal generating agent) which can be used in the present invention.
Figure 2:
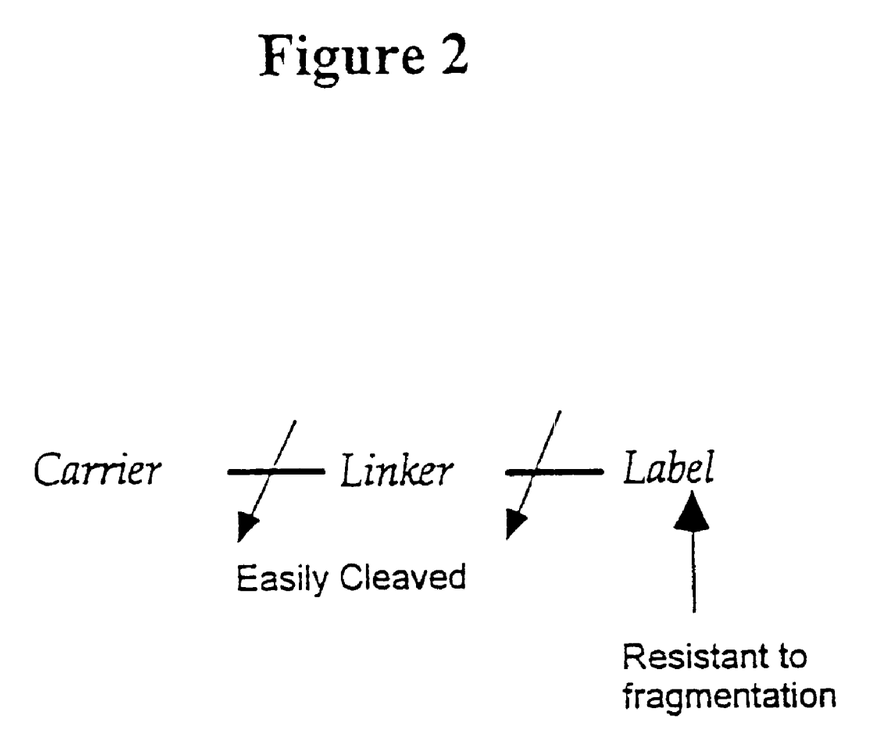
FIG. 2 shows a label precursor in further detail.
Figure 3:
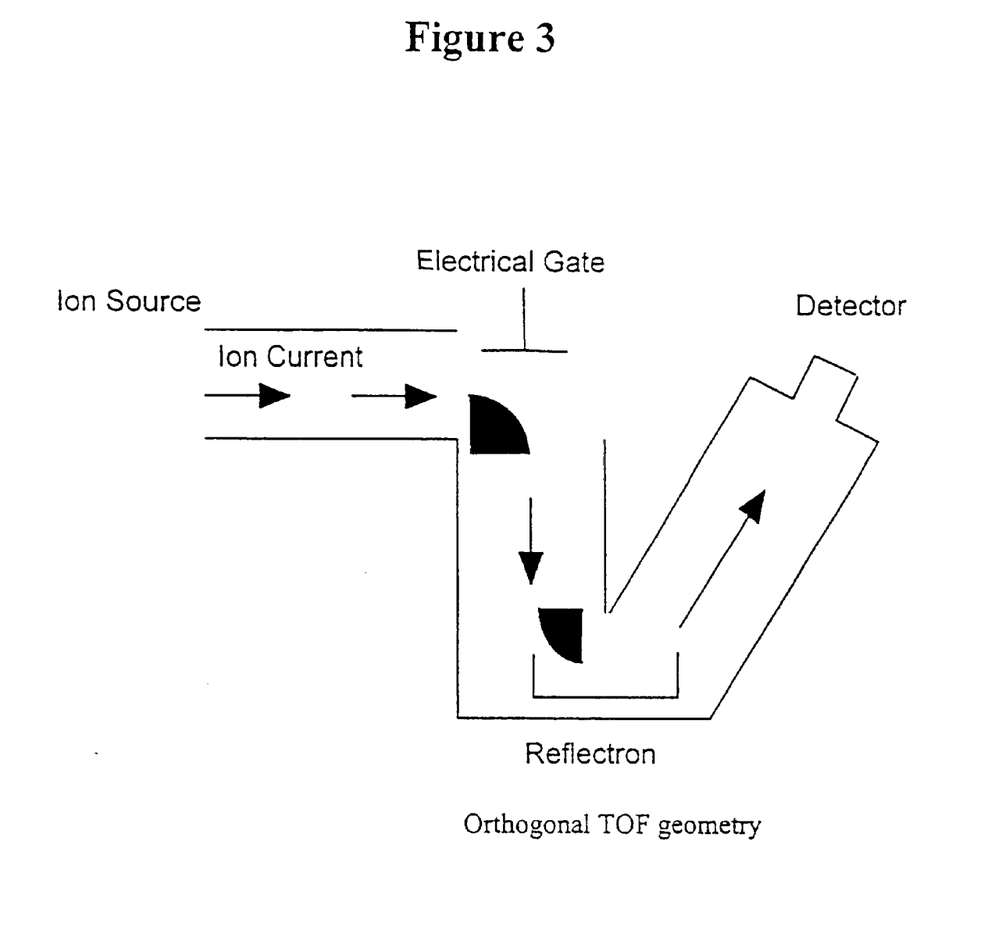
FIG. 3 shows an arrangement for carrying out orthogonal time-of-flight mass spectrometry, which can be used in conjunction with the present invention.

A technology that will permit amplification of a signal in a non-radioactive manner and which permits very many labels to be used simultaneously is described here. Such a system requires probes to be labelled with catalytic agents that will cleave a specific chemical bond, or a bond in a specific molecular environment. A signal is generated by the cleavage of a secondary molecule which comprises a mass label, bonded by a specifically cleavable linker to a carrier molecule. The mass label identifies the linker that is cleaved. In an array of probes labelled with catalysts, only one catalytic cleavage agent should cleave any single linker. Thus the mass label identifies the corresponding probe. An array of secondary molecules is thus required, one for each probe with a unique linker and a unique mass label identifying each secondary molecule.

Typical assays involving probes of this form would be similar in principal to those used in colorimetric or fluorescence based systems. Labelled probe is added to target molecules in a sample where binding takes place. Bound probe is separated from unbound probe and then the presence of bound probe is assayed.

Numerous systems exist to separate labelled probe from unlabelled probe. The method used will depend largely on the nature of the probe target interactions. Some systems will be discussed here by way of example but these are by no means limiting.

Assaying the presence of bound probe is effected with this system by adding a known quantity of the secondary carrier molecule linked to its corresponding mass label. Any given bound probe will carry a catalytic cleavage agent suitable to cleave a specific linker releasing a corresponding mass label. The catalyst can liberate a massive quantity of label in a given time and can thus generate a significant amplification of signal.

Probe Molecules

Probe molecules include but are not limited to antibodies, oligonucleotides, peptides and proteins, including enzymes, RNA aptamers, dextrans.

Catalytic Agents

Catalytic agents include but are not limited to protein enzymes, catalytic RNA molecules, organic catalysts.

Favourable enzyme systems include hydrolytic enzymes such as lysozyme, trypsin, chymotrypsin, elastase, alkaline phosphatase, peroxidases. Restriction endonucleases would be an excellent class of enzymes to exploit for non-DNA target molecules as oligonucleotide linkers bearing the recognition sequence for a specific endonuclease would allow a significant number of carrier molecules to be generated.

'Secondary' Signal Generating Agents

Secondary agents comprise a mass label, cleavably linked to a carrier molecule via a linker that is cleaved specifically by a catalytic agent. The mass label identifies the linker used. This in turn should be specific to only one catalyst in any given assay thus allowing liberation of mass label from its carrier to be related back to the presence of a single probe molecule.

Carrier Molecules

Carrier molecules must be capable of being readily linked to cleavable linker groups. A single carrier should be able to be linked to all or as many as possible of available linkers to allow combinatorial reuse of carrier molecules. Furthermore a single carrier could be derivitised with multiple linker groups coupled to mass labels to give a high density of secondary agent from which to generate a large signal.

One could for example derivitise all the exposed amine residues of a small protein, or one could target carboxyl and hydroxyl groups with a linker group as these are all groups that can be fairly readily derivitised.

Carrier molecules should not inhibit cleavage reactions and should be easily separable from cleaved mass labels. Mass spectrometry facilitates this separation. In a simple case the carrier molecule need only be chosen to fall outside the mass range of mass labels. For example, if the mass range in which mass labels are designed to occur is up to a mass charge ratio of 2000, then the carrier molecule would be chosen to have a mass/charge ratio of greater than 2000. Furthermore, it should be resistant to fragmentation to ensure that fragmentation products do not coincide with mass label peaks.

A potentially simpler alternative supported by mass spectrometry is to choose a carrier molecule that takes a different charge from the mass labels. Thus if mass labels that become negatively charged on ionisation are used then a carrier that becomes positively charged is appropriate. However, carrier that is still linked to uncleaved mass label, should preferably also take a net positive charge to facilitate separation of labels from uncleaved carrier.

Separation outside the mass spectrometer is also possible. Carrier molecules could be as simple as biotin cleavably linked to a mass label. This would permit uncleaved carrier to be easily separated from cleaved mass labels by an avidin affinity column. Clearly any immobilisation system could be used, including but not limited to poly-histidine metal coordination systems, photocross-linking agents, antibodies, RNA aptamers, oligonucleotides, etc.

Linkers

Linker groups should permit specific cleavage by a single catalytic agent from a family of such agents used in a multiplexed probing reaction.

Saccharides of N-acetyl glucosamine (GlcNAc) are an effective substrate for lysozyme as are alternating oligosaccharides of N-acetyl muramic acid and GlcNAc, particularly hexasaccharides of each.

The serine proteases are a class of enzymes with fairly distinct specificities. Trypsin will cleave peptide bonds only after lysine or arginine residues. Chymotrypsin will cleave only after large hydrophobic residues. Thus peptide linkers with these distinct features would be appropriate to use with their corresponding enzyme.

Restriction endonucleases have very high specificity for their substrate, have a very diverse array of substrates and are manufactured in quantity for reasonable prices. Eco RI cuts at the sequence 5'-GAATTC-3', while Hind III cuts at 5'-AAGCTT-3' and Hpa I cuts at 5'-GTTAAC-3'. Thus with a group of restriction enzymes as catalytic markers on a probe molecule, one could use oligonucleotides as linkers. An oligonucleotide biotinylated at one terminus and bearing a mass label at the other terminus would be a relatively simple reagent to produce. This sort of system would not be appropriate for use with DNA targets.

Gene Profiling Using Catalytically Generated Mass Labels

Gene expression profiling techniques often fail to detect mRNAs expressed at very low levels. Most gene expression profiling techniques require conversion of mRNA into cDNA before assaying for particular sequences. Certain mRNAs are missed in the reverse transcription process. Low level mRNAs that are reverse transcribed into cDNAs are still at very low levels and may be missed by the assaying technique. Differential display techniques and arbitrarily primed reverse transcription techniques use sets of primers, usually fluorescently or radiolabelled primers to generate fragments of cDNA of specific lengths. The primer sets are designed statistically to prime as many mRNAs as possible with as few primers as possible. To detect the fragments generated by each primer in a mixed reaction is not really possible in conventional techniques so primers must be spatially resolved which means a separate reaction vessel for each primer or set of primer to be followed independently. If single assays could be performed where each primer can labelled independently then significant savings in reagents, manpower and time would be achieved. This invention permits individually labelled primers to be used.

For assaying specifically for low levels of specific mRNAs for which specific primer pairs are available this technology is well suited. One could label one primer for each pair with an immobilisation agent such as biotin. The second primer could be labelled with a unique catalyst. mRNA or single stranded cDNA could be primed with the first primer and the primed template can be extended by a reverse transcriptase or polymerase respectively. The double stranded product can then be immobilised, if the primer is not already immobilised. One can achieve linear amplification of the template with further cycles of denaturation and priming with the first primer. The double stranded products are then denatured and the free strands, unused primer, etc. is washed away leaving immobilised single stranded template. The second primer can be added at this stage to prime the immobilised strand and can be extended by a polymerase. Unincorporated primer is washed away after synthesis of the second strand. Incorporation of the second primer can then be assayed by addition of cleavable mass label carriers. Clearly many mRNAs can be assayed for simultaneously in a system like this.

Oligonucleotide Ligase Assays

The oligonucleotide ligase assay is a technique for fast genotyping. The principle is simple for—a given single nucleotide polymorphism (SNP), two oligonucleotides are necessary. One immediately complementary to a region 5' of the SNP and one adjacent to the 5' oligonucleotide which overlaps the SNP. The 5' oligonucleotide is typically biotin labelled, while the 3' oligonucleotide is typically fluorescently labelled, 1 dye is used to identify each of the 4 possible bases that the SNP might adopt. An amplified clone of a gene or DNA fragment of interest is assayed in a ligase reaction. The 5' and 3' oligonucleotides are allowed to hybridise to their complementary sequences in the target DNA in the presence of ligase. The 3' oligonucleotide complementary to the SNP bearing sequence should be preferentially ligated to the 5' oligonucleotide over the other 3 possible oligonucleotides. The ligation can be assayed by capturing the 5' oligonucleotides onto an avidinated substrate and determining the quantity and frequency of fluorescence generated by the ligated 3' oligonucleotide.

The small number of commercially available fluorescent dyes is a limit on this system being extended to determine the nature of multiple SNPs in a large gene such as the cystic fibrosis gene. Using catalytically cleavable mass labels and corresponding catalyst labelled oligonucleotides would permit a multiplexed reaction wherein numerous SNPs in a single gene could be assayed for.

Features of Mass Labels

To achieve the required behaviour from a mass label, certain chemical properties are desirable. These are represented in particular molecular groups or moieties that can be incorporated into mass labels in a number of ways.

For the purposes of generating mass labels, favoured labels require a specifically cleavable bond in the linker and fragmentation resistant bonds in the mass label.

For optimal performance using present techniques a mass/charge ratio of up to 2000 to 3000 units is the optimal range for such labels as this corresponds to the range over which singly charged entities can be reliably detected with greatest sensitivity, however labels of mass less than 100 to 200 daltons are not ideal as the low mass end of the spectrum tends to be populated by solvent molecules, small molecule impurities, multiple ionisation peaks and fragmentation peaks.

To permit detection one requires labels that have a net charge, but are preferably not multiply ionisable, i.e. they have a fixed single charge. Furthermore they should be resistant to fragmentation. This ensures that each peak in the mass/charge spectrum corresponds to a single label and simplifies the analysis of the data. Furthermore this reduces any ambiguity in the determination of the quantity of the label, which is very important for some of the applications for which this invention has been developed.

Various functionalities exist which carry or can carry positive charges for positive ion mass spectrometry. These include but are not limited to amines particularly tertiary amines and quaternary amines. Quaternary ammonium groups carry a single positive charge and do not require ionisation. For positive ion spectrometry these allow great sensitivity. Hence preferred positive ion mass labels should carry at least one such group.

Various functionalities are available to carry a negative charge for negative ion mass spectrometry which include but are not limited to carboxylic acids, phosphonates, phosphates, phenolic hydroxyls, sulphonic acids, sulphonilamides, sulphonyl urea, tetrazole and perfluoro alcohol.

Ionisation Techniques

For many biological mass spectrometry applications so called 'soft' ionisation techniques are used. These allow large molecules such as proteins and nucleic acids to be put into the mass spectrometer in solutions with mild pH and at low concentrations. Two such techniques are ideal for use with this invention; electrospray ionisation and Matrix Assisted Laser Desorption Ionisation (MALDI).

Electrospray Ionisation

Electrospray ionisation requires that the dilute solution of biomolecule be 'atomised' into the spectrometer, i.e. in a fine spray. The solution is, for example, sprayed from the tip of a needle across an electrostatic field gradient or into a stream of dry nitrogen in an electrostatic field. The mechanism of ionisation is not fully understood but is thought to work broadly as follows. In a stream of nitrogen the solvent is evaporated. With a small droplet, this results in concentration of the biomolecule. Given that most biomolecules have a net charge this increases the electrostatic repulsion of the dissolved protein. As evaporation continues this repulsion ultimately becomes greater than the surface tension of the droplet and the droplet 'explodes' into smaller droplets. The electrostatic field helps to further overcome the surface tension of the droplets. The evaporation continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber through a pair of electrodes. The potential difference across these electrodes determines whether positive or negative ions pass into the mass analyser and also the energy with which these ions enter the mass spectrometer. This is of significance when considering fragmentation of ions in the mass spectrometer. The more energy imparted to a population of ions the more likely it is that fragmentation will occur. By adjusting the accelerating voltage used to accelerate ions from the ionisation chamber one can control the fragmentation of ions.

Matrix Assisted Laser Desorption Ionisation (MALDI)

MALDI requires that the biomolecule solution be embedded in a large molar excess of an photo-excitable 'matrix'. The application of laser light of the appropriate frequency (266 nm beam for nicotinic acid) results in the excitation of the matrix which in turn leads to excitation and ionisation of the embedded biomolecule. This technique imparts a significant quantity of translational energy to ions, but tends not to induce excessive fragmentation despite this. Accelerating voltages can again be used to control fragmentation with this technique though.

MALDI techniques can be supported in two ways. One can embed mass labelled DNA in a MALDI matrix, where the labels themselves are not specifically excitable by laser or one can construct labels that contain the necessary groups to allow laser energisation. The latter approach means the labels do not need to be embedded in a matrix before performing mass spectrometry. Such groups include nicotinic, sinapinic or cinnamic acid moieties. MALDI based cleavage of labels would probably be most effective with a photocleavable linker as this would avoid a cleavage step prior to performing MALDI mass spectrometry. The various excitable ionisation agents have different excitation frequencies so that a different frequency can be chosen to trigger ionisation from that used to cleave the photolysable linker. These excitable moieties are easily derivitised using standard synthetic techniques in organic chemistry so labels with multiple masses can be constructed in a combinatorial manner.

Fragmentation Within the Mass Spectrometer

Fragmentation is a highly significant feature of mass spectrometry. With respect to this invention it is important to consider how one intends to identify a mass label. At the two extremes one can either design molecules that are highly resistant to fragmentation and identify a label by the appearance of the label's molecular ion in the mass spectrum. One would thus design families of labels to have unique molecular ions. At the other extreme one can design a molecule with a highly characteristic fragmentation pattern that would identify it. In this case one must design families of labels with non-overlapping patterns or with at least one unique fragmentation species for each label by which to identify each label unambiguously. Fragmentation is, however, a property of the molecule and of the ionisation technique used to generate the ion. Different techniques impart differing amounts of energy to the ion and the chemical environment of the ions will vary considerably, thus labels that are appropriate for one mass spectrometry technique may be inappropriate in others. The preferred approach is to design fragmentation resistant molecules, although some fragmentation is inevitable. This means one aims to identify molecules with a single major species, either the molecular ion or a single very highly populated fragment ion.

Determining Bond Stability in the Mass Spectrometer

In neutral molecules it is reasonably simple to determine whether a molecule is resistant to fragmentation, by consideration of bond strengths. However, when the molecule is ionised, the bond strength may increase or decrease in ways that are difficult to determine a priori. For example, given a bond, X—Y, we can write:

un-ionised:

$$X\text{—}Y \rightarrow X^+ + Y^+$$

$$\therefore D(X\text{—}Y) = \Delta H(X^+) + \Delta H(Y^+) - \Delta H(X\text{—}Y)$$

But $$D(X\text{—}Y)^+ = \Delta H(X^+) + \Delta H(Y^+) - \Delta H(X\text{—}Y^+)$$

$$\therefore D(X\text{—}Y) - D(X\text{—}Y)^+ = \Delta H(X^+) - \Delta H(X^+)$$

$$- \Delta H(X\text{—}Y) - \Delta H(X\text{—}Y^+)$$

and $$I(X^+) = \Delta H(X^+) - \Delta H(X^+)$$

$$I(X\text{—}Y) = \Delta H(X\text{—}Y^+) - \Delta H(X\text{—}Y)$$

$$\therefore D(X\text{—}Y) - D(X\text{—}Y)^{30} = I(X\text{—}Y) - I(X^+)$$

This means $D(X\text{—}Y) - D(X\text{—}Y)^+ > 0$ if $I(X\text{—}Y) > I(X^+)$

Similarly $D(X\text{—}Y) - D(X\text{—}Y)^+ < 0$ if $I(X\text{—}Y) < I(X^+)$ since both $I(X\text{—}Y)$ and $I(X^+)$ are positive.

In the equations above, D(A—B) refers to bond energy of the species in parentheses, I(N) refers to the ionisation energy of the species in parentheses and delta-H is the free energy of formation of the species in parentheses. The upshot of the equations above is that in order to predict whether a bond is likely to be stable under a given set of ionisation conditions we need to know the energy of ionisation of the molecule and the energy of ionisation of the neutral fragment that results from fragmentation at the bond in question.

For example, consider the C—N bond in aniline:

$$I(NH_2^+) = 11.14 \text{ electronvolts (ev) and } I(C_6H_5NH_2) = 7.7 \text{ ev}$$

$$\therefore I(C_6H_5NH_2) < I(NH_2^+) \text{ by } 3.44 \text{ ev}$$

The alternative cleavage at this bond is:

$$I(C_6H_5^+) = 9.35 \text{ electronvolts (ev) and } I(C_6H_5NH_2) \ 7.7 \text{ ev}$$

$$\therefore I(C_6H_5NH_2) < I(C_6H_5^+)$$

This bond is thus not easily broken in the ion. Aniline, if it has sufficient initial energy to fragment, is generally observed to cleave releasing HCN, rather than by cleavage of a C—N bond. Similarly considerations apply to phenol:

$$I(OH^+) = 13 \text{ ev and } I(C_6H_5OH) = 8.47 \text{ ev}$$

$$\therefore I(C_6H_5OH) < I(OH^+)$$

The alternative cleavage at this bond is $$I(C_6H_5^+) = 9.35 \text{ ev and } I(C_6H_5OH) = 8.47 \text{ ev}$$

$$\therefore I(C_6H_5OH) < I(C_6H_5^+)$$

Thus C—O cleavage is not observed.

Determining the differences in ionisation energies of molecule and neutral fragments is a general working principle which can be used to predict likely ion bond strengths. If the energy added during ionisation is less than the ionic bond strength then ionisation will not be observed. Typical ionic bonds that have good strength include, aryl-O, aryl-N, aryl-S bonds. Generally, aliphatic type bonds become less stable in ionic form. Thus single C—C bonds are weak in the ion but C═C is still strong. Aryl-C═C tends to be strong too for the same reasons as aryl-O, etc. Aryl or Aryl-F bonds are also strong in ionic form which is appealing as fluorocarbons are cheap to manufacture and are chemically inert.

Similar considerations apply to negative ions, except one must use electron affinities in the equations above rather than ionisation energies.

Mass Label Chemistries

For any practically or commercially useful system it is important that construction of labels be as simple as possible using as few reagents and processing steps as possible. A combinatorial approach in a which a series of monomeric molecular units are available to be used in multiple combinations with each other would be ideal.

One can synthesise mass labels using standard organic chemistry techniques. Such labels ought to carry a single charge bearing group and should be resistant to fragmentation in the mass spectrometry technique used. Amine derivatives, quaternary ammonium ions or positive sulphur centres are good charge carriers if positive ions mass spectrometry is used. These have extremely good detection properties that generate clean sharp signals. Similarly, negatively charged ions can be used, so molecules with carboxylic acid, sulphonic acid and other moieties are appropriate for negative ion spectrometry. Labels for MALDI mass spectrometry can be generated by derivitising known molecules that are excitable by UV laser light, such as sinapinnic acid or cinnamic acid, of which a number of derivatives are already commercially available. Fragmentation resistant groups are discussed above. For a text on organic chemistry see:

Vogel's "Textbook of Organic Chemistry" 4th Edition, Revised by B. S. Furniss, A. J. Hannaford, V. Rogers, P. W. G. Smith & A. R. Tatchell, Longman, 1978.

Amino Acids

With a small number of amino acids such as glycine, alanine and leucine, a large number of small peptides with different masses can be generated using standard peptide synthesis techniques well known in the art. With more amino acids many more labels can be synthesised.

E. Atherton and R. C. Sheppard, editors, 'Solid Phase Peptide Synthesis: A Practical Approach', IRL Press, Oxford.

Carbohydrates

Similarly carbohydrate molecules are useful monomeric units that can be synthesised into heteropolymers of differing masses but these are not especially amenable to ESMS.

Gait, M. J. editor, 'Oligonucleotide Synthesis: A Practical Approach', IRL Press, Oxford, 1990

Eckstein, editor, 'Oligonucleotides and Analogues: A Practical Approach', IRL Press, Oxford, 1991

Other Labelling Chemistries

Clearly almost any molecule can be tacked onto another as a label. Obviously the properties of such labels in the mass spectrometer will vary. In terms of analysing biomolecules it will be important that the labels be inert, bear a single charge and be resistant to fragmentation.

Quantification and Mass Spectrometry

For the most part biochemical and molecular biological assays are quantitative. The mass spectrometer is not a simple device for quantification but use of appropriate instrumentation can lead to great sensitivity. It must always be remembered that the ion count is not a direct measure of the source molecule quantity, the relationship is a complex function of the molecule's ionisation behaviour. Quantitation is effected by scanning the mass spectrum and counting ions at each mass/charge ratio scanned. The count is integrated to give the total count at each point in the spectrum over a given time. These counts can be related back to the original qunatities of source molecules in a sample. Methods for relating the ion count or current back to the quantity of source molecule vary. External standards are one approach in which the behaviour of the sample molecules is determined prior to measurement of unknown sample. A calibration curve for each sample molecule can be determined by measuring the ion current for serial dilutions of a sample molecule when fed into the instrument configuration being used.

Internal standards are probably the more favoured approach rather than external standards, since an internal standard is subjected to the same experimental conditions as the sample so any experimental vagaries will affect both internal control and sample molecule. To determine the quantity of a sample molecule, an internal standard of a known quantity is added to the sample. The internal standard is chosen to have a similar ionisation behaviour as the molecule being measured. Thus the ratio of sample ion count to standard ion count can be used to determine the quantity of sample as the ratio of qunatities should be the same. Choosing appropriate standards is the main difficulty with this approach. One must find a molecule that is similar but not identical in its mass spectrum. A favourable approach is to synthesise the sample molecule with appropriate isotopes to give a slightly different mass spectrum, for a molecule with the same chemical behaviour. This approach might be less desirable than external standards for use with large numbers of mass labels due to the added expense of finding or synthesising appropriate internal standards but will give better qunatification than external standards. An alternative to isotope labelling is to identify a molecule that has similar but not identical chemical behaviour as the sample in the mass spectrometer. Finding such analogues is difficult and is a significant task for large families of mass labels.

A compromise approach might be appropriate though, since large families of mass labels will ideally be synthesised combinatorially, and will thus be related chemically. A small number of internal controls might be used, where each individual control determines the quantities of a number of mass labels. The precise relationship between internal standard and each mass label might be determined in external calibration experiments to compensate for any differences between them.

The configuration of the instrument is critical to determining the actual ion count itself, particularly the ionisation method and the separation method used. Certain separation methods act as mass filters like the quadrupole which only permits ions with a particular mass charge ratio to pass through at one time. This means that a considerable proportion of sample never reaches the detector. Furthermore most mass spectrometers only detect one part of the mass spectrum at a time. Given that a large proportion of the mass spectrum may be empty or irrelevant but is usually scanned anyway, this means a further large proportion of the sample is wasted. These factors may be a problem in detecting very low abundance ions but these problems can in large part be overcome by correct configuration of the instrumentation.

To ensure better quantification one could attempt to ensure all ions that are generated are detected. Mattauch-Herzog geometry sector instruments permit this but have a number of limitations. Sector instruments are organised into distinct regions, 'sectors', that perform certain functions. In general the ionisation chamber feeds into a free sector which feeds into an 'electric sector'. The electric sector essentially 'focuses' the ion beam which is divergent after leaving the ion source. The electronic sector also ensures the ion stream has the same energy. This step results in the loss of a certain amount of sample. This focused ion beam then passes through a second free area into a magnetic sector which splits the beam on the basis of its mass charge ratio. The magnetic sector behaves almost like a prism. A photographic plate can be placed in front of the split beam to measure the intensities of the spectrum at all positions. Unfortunately there is a limit on the dynamic range of these sorts of detector and it is messy and cumbersome. Better dynamic range is achievable with electron multiplier arrays, but at a cost of loss in resolution which is limited by how close together the elements of the array can be constructed. With a family of well characterised mass labels one would probably monitor only sufficient peaks to sample all the mass labels unambiguously. In general array detectors would allow one to simultaneously and continuously monitor a number of regions of the mass spectrum simultaneously, which might be applicable for use with well characterised mass label families. The limit on the resolution of closely spaced regions of the spectrum might restrict the number of labels one might use, though, if array detectors are chosen. For 'selected ion monitoring' (SIM) the quadropole has an advantage over many configurations in that the fields that filter ions can be changed with extreme rapidity allowing a very high sampling rate over a small number of peaks of interest.

Orthogonal TOF Mass Spectrometry

An approach that is preferable to array geometries is the orthogonal time of flight mass spectrometer. This geometry that allows for very fast sampling of an ion stream followed by almost instantaneous detection of all ion species. The ion current leaving the source, probably an electrospray source for many biological applications, passes an electrode plate perpendicular to the current. This plate is essentially an electrical gate and is used to generate a repulsive potential which deflects the ion current 'orthogonally' into a time of flight mass analyser that uses a reflectron. The reflectron is essentially a series of circular electrodes that generate an increasingly repulsive electromagnetic field that normalises ion energies and reflects the ion stream into a detector. The reflectron is a simple device that greatly increases the resolution of TOF analysers. Ions leaving the ion source will have different energies, faster ions will penetrate the repulsive field further than ions with a lower energy and so will be delayed slightly with respect to the lower energy ions but since they will arrive slightly before the lower energy ions they will enter the TOF at roughly the same time so all the ions of a given mass charge ratio will arrive at the detector at roughly the same time. When the electrical gate is 'closed' to deflect ions into the TOF analyser, the timer is triggered. The flight time of the deflected ions is recorded and this is sufficient to determine their mass/charge ratio. The gate generally only sends a short pulse of ions into the TOF analyser at any one time. Since the arrival of all ions is recorded and since the TOF separation is extremely fast, the entire mass spectrum is measured effectively simultaneously. Furthermore, the gate electrode can sample the ion stream at extremely high frequencies so very little sample is required. For these reasons this geometry is extremely sensitive, to the order of a few femtomoles.

Mass labels that can be used in the present invention include those disclosed in GB 9700746.2, GB 9718255.4, GB 9726953.4, PCT/GB98/00127 and the UK application having Page White and Farrer file number 87820. The contents of these applications are incorporated herein by reference.

Specific methods for gene profiling in which the method of the present invention can be used are disclosed in PCT/GB98/01134 and the PCT application having Page White and Farrer file number 88061. The contents of these applications are incorporated herein by reference.

What is claimed is:

1. A method for assaying for a substance, which method comprises the following steps:
   (i) contacting the substance with an assay agent comprising a probe and a catalytic agent, wherein said probe binds to the substance;
   (ii) separating said probe which has bound to the substance from said probe which has not bound to the substance;
   (iii) contacting said substance bound to said probe with a label precursor, wherein said label precursor reacts catalytically with said catalytic agent to release a mass label;
   (iv) detecting the mass label by mass spectrometry, thereby assaying for the substance.

2. The method according to claim 1, wherein the catalytic agent is capable of cleaving a specific chemical bond, or a bond in a specific molecular environment.

3. The method according to claim 1, in which the label precursor comprises a label attached to a carrier moiety via a linker, the label being specific to the linker, and wherein the linker is capable of being cleaved by a specific catalytic agent to release the label.

4. The method according to claim 3, wherein the carrier moiety is selected such that it allows the label precursor to be captured on a solid phase.

5. The method according to claim 4, wherein the carrier moiety comprises biotin for attaching the label precursor to an avidinated solid phase.

6. The method according to claim 1, wherein the probe is selected from the group consisting of an antibody, an oligonucleotide, a protein, a peptide, an enzyme, an RNA aptamer, a dextran, and combinations thereof.

7. The method according to claim 1, wherein the catalytic agent is selected from the group consisting of an organic catalyst, a protein enzyme, a catalytic RNA molecule, and combinations thereof.

8. The method according to claim 7, wherein the catalytic agent comprises a hydrolytic enzyme.

9. The method according to claim 1, wherein the catalytic agent comprises an endonuclease and the label precursor comprises an oligonucleotide linker capable of being cleaved catalytically by the endonuclease to release the label.

10. A method for assaying for the presence of a plurality of substances in a mixture, which method comprises the following steps:
    (i) contacting the mixture with an assay agent comprising an array of probes, wherein each probe comprises a catalytic agent specific to that probe, to bind each substance in the mixture with a probe and thus a catalytic agent specific to that substance;
    (ii) separating said probes which have bound to a substance from said probes which have not bound to a substance;
    (iii) contacting the substances which have bound to a probe with an array of label precursors, wherein each label precursor reacts catalytically with a catalytic agent specific to that precursor to release a mass label specific to its precursor;
    (iv) detecting the mass label by mass spectrometry, thereby assaying for the presence of the substances.

11. The method according to claim 10, wherein each label precursor comprises a label attached to a carrier moiety via a linker and the carrier moiety of each label precursor is selected such that it has a different mass to each of the mass labels in the array of label precursors.

12. The method according to claim 8, wherein said hydrolytic enzyme is selected from the group consisting of lysozyme, trypsin, chymotrypsin, an elastase, an alkaline phosphitase and a peroxidase.

13. A method for detecting one or more mRNA moieties comprising the following steps:
    (i) contacting the mRNA(s) with an assay agent comprising a probe and a catalytic agent, wherein said probe binds to the mRNA(s);
    (ii) separating said probe which has bound to the mRNA(s) from said probe which has not bound to the mRNA(s);
    (iii) contacting said mRNA(s) bound to said probe with a label precursor, wherein said label precursor reacts catalytically with said catalytic agent to release a mass label;
    (iv) detecting the mass label by mass spectrometry, thereby assaying for the mRNA(s).

* * * * *

UNITED STATES PATENT AND TRADEMARK OFFICE
CERTIFICATE OF CORRECTION

PATENT NO.   : 6,649,354 B1
DATED        : November 18, 2003
INVENTOR(S)  : Gunter Schmidt and Andrew Hugin Thompson

It is certified that error appears in the above-identified patent and that said Letters Patent is hereby corrected as shown below:

<u>Title page,</u>
Item [86], please correct the section under "§ 371" to read as follows:

-- § 371 (c)(1), (2), (4) Date:  May 3, 2000 --

Signed and Sealed this

Sixth Day of April, 2004

JON W. DUDAS
*Acting Director of the United States Patent and Trademark Office*